United States Patent [19]

Diemeer et al.

[11] Patent Number: 4,596,443

[45] Date of Patent: Jun. 24, 1986

[54] LIGHT GUIDE FOR LIQUID DETECTION AND CABLE COMPRISING SUCH A GUIDE

[75] Inventors: Martinus B. J. Diemeer; Alphonsus G. W. M de Jongh, both of Zoetermeer, Netherlands

[73] Assignee: Staat der Nederlanden (Staatsbedrifj der Posterijen, Telegrafie en Telefonie), The Hague, Netherlands

[21] Appl. No.: 724,048

[22] Filed: Apr. 18, 1985

Related U.S. Application Data

[63] Continuation of Ser. No. 464,899, Feb. 8, 1983.

[30] Foreign Application Priority Data

Feb. 9, 1982 [NL] Netherlands ............... 8200495

[51] Int. Cl.⁴ ............................... G02B 6/44
[52] U.S. Cl. ................. 350/96.23; 174/96
[58] Field of Search .......... 350/96.23; 174/96, 98, 174/118

[56] References Cited

U.S. PATENT DOCUMENTS

| | | | |
|---|---|---|---|
| 3,786,681 | 1/1974 | Kiehn | 73/382 |
| 3,931,518 | 1/1976 | Miller | 250/227 |
| 4,019,051 | 4/1977 | Miller | 250/227 |
| 4,118,594 | 10/1978 | Arnaud | 350/96.23 |
| 4,270,049 | 5/1981 | Tanaka et al. | 250/227 |
| 4,361,381 | 11/1982 | Williams | 350/96.23 |
| 4,401,366 | 8/1983 | Hope | 350/96.23 |
| 4,419,157 | 12/1983 | Ferrentino | 174/118 |

FOREIGN PATENT DOCUMENTS

| | | |
|---|---|---|
| 2508315 | 2/1975 | Fed. Rep. of Germany . |
| 2842077 | 9/1978 | Fed. Rep. of Germany . |
| WO79/00377 | 6/1979 | PCT Int'l Appl. . |

OTHER PUBLICATIONS

Applied Physics Letters, vol. 30, No. 10, May 15, 1980 (New York) J. N. Fields "Attenuation of a Parabolic-Index Fiber with Periodic Bends" pp. 799-801.

*Primary Examiner*—William L. Sikes
*Assistant Examiner*—Akm E. Ullah
*Attorney, Agent, or Firm*—Hugh Adam Kirk

[57] ABSTRACT

A glass-fibre cable has been provided with a signalling conductor for signalling liquid which has penetrated into the cable sheath. The signalling conductor is a glass fibre, which is inserted in a protective perforated sheath in the usual way. The inner periphery of this sheath is provided with a wave-shaped pattern on one side, whereas the opposite side is provided with a layer of swelling powder. As soon as the liquid which has entered the cable, reaches the swelling powder, the volume of this swelling powder will considerably increase, in consequence of which the glass fibre will be pressed against the wave-shaped pattern. This causes microbending which involves a strong, measurable attenuation of the light signal transmitted through the glass fibre. The swelling powder can be applied to a substrate.

6 Claims, 5 Drawing Figures

LIGHT GUIDE FOR LIQUID DETECTION AND CABLE COMPRISING SUCH A GUIDE

This is a continuation of co-pending application Ser. No. 464,899 filed on Feb. 8, 1983.

BACKGROUND OF THE INVENTION

The inventon relates to a signalling conductor. Signalling conductors are frequently used in cables for signalling when liquid has been penetrated into the cable.

According to an earlier proposal, an electrically conducting wire is included in a cable, which mainly comprises light guides, which wire is at the same time used for signalling liquid, such as ground water, which may have penetrated into the cable. From a production technical point of view the inclusion of electric conductors with a plurality of optical conductors arranged in a cable encounters difficulties.

SUMMARY OF THE INVENTION

The present invention comprises a signalling conductor with a light guide instead of an electric guide. This offers the possibility of including a signalling conductor in a cable with light guides in a way which is, from an economic point of view, more attractive than the way used hitherto. This is achieved by a tubular element, which is pervious to liquid and which contains besides a light guide, a material which swells under the influence of liquid. Now when liquid enters the tubular element, the light guide will be slightly deformed between the swelling material and the wall of the tubular element which deformation is detectable as an attenuation in the signal passing through said light guide.

In a preferred embodiment, the tubular element can be provided with a pressure area formed in such a way that microbending will occur, when the light guide is deformed. The effects of microbending of light guides are described in the article by J. N. Fields in the journal "Applied Physics Letters" 36(10), May 15, 1980, pp. 799–801.

The deformation of the light guide can be ascertained in a simple way, and also the place where the liquid which has entered the cable, can be located.

The invention will be further elucidated hereinafter with reference to the drawing, in which FIGS. 1a and 1b are cross-sectional views of a preferred embodiment of a signalling conductor according to the invention showing without and with liquid in the section, respectively;

Figure 1A:
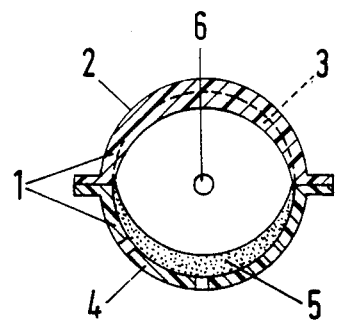

FIG. 1a shows a sectional view of a preferred embodiment, in which 1 designates a tubular element, here designed with an upper part 2 comprising a wave-shaped pattern 3, and a lower perforated part 4 containing a swelling powder 5. A light guide 6 is mainly inserted loose in the tubular element 1. The parts 2 and 4 can be made of a suitable synthetic material, such as polyvinyldifluoride (PVDF). The wave-shaped pattern 3, the rib structure of which is in a position transversely to the longitudinal direction, can be rolled in in the course of the moulding process of the upper part 2. The swelling powder 5 in the lower part 4 can have the form of an emulsion or it can be applied to a suitable substrate, such as a non-woven glass-fibre strip. After the light guide 6 has been inserted, the parts 2 and 4 are rolled on the edges to seal them together.

For each unit of length of the tubular element 1 the quantity of swelling powder supplied should be such that when liquid is absorbed, the light guide in the relevant portion will be deformed, due to the expansion of the swelling powder, to such an extent that signalling can take place, whereas the tubular element itself remains intact. The volume of a suitable swelling powder increases about 20 times when wet. The absorption of liquid takes place e.g. through the perforations in the lower part 4 and/or in the upper part 2.

Figure 1B:
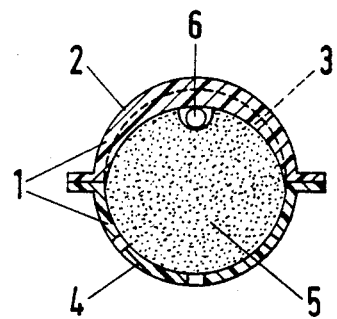

FIG. 1b shows a sectional view of the same optical guide as in FIG. 1a after the absorption of liquid. The swelling powder 5 has filled the tubular element 1 almost entirely and presses the light guide 6 against the wave-shaped pattern 3. It is remarked that even when the tubular element is not provided with a wave-shaped pattern, the structure of the light guide 6 produces an observable attenuation of the light signal in the light guide 6 of at least 0.5 dB/m. If the light guide is pressed on such a wave-shaped pattern that microbending can be caused, an attenuation to 10 dB may be measured when liquid is absorbed over a distance of about 10 cm length of the cable.

The attenuation and the place where the liquid enters can be measured according to known methods, such as by the back-scatter method.

Figure 2:
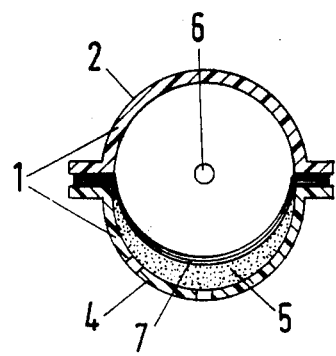
FIG. 2 is a cross sectional view of a another embodiment of a signalling conductor with separated compartments for light guide and swelling material.

When it is undesirable that the light guide 6 should come into direct contact with entering liquid, the embodiment according to FIG. 2 may be used. A flexible membrane 7, which can be provided with a wave-shaped pattern 3, is mounted between the swelling powder 5 and the space containing the light guide 6.

Figure 3:
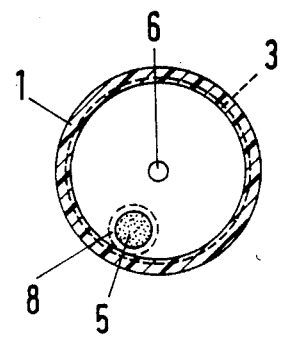
FIG. 3 is a cross sectional view of still another embodiment of a signalling conductor with swelling material applied to a round substrate.

FIG. 3 shows a third embodiment in which the whole inner periphery of the tubular element 1 is provided with the wave-shaped pattern 3, which can have the shape of separate ribs as well as the shape of a helical rib or groove with a suitable pitch. The swelling powder 5 is here applied to a rolled-up supporting layer or substrate 8, which can be easily included in the tubular element 1 in the course of its manufacture. When liquid enters, the substrate 8 can unroll filling the space in the tubular element 1.

Figure 4:
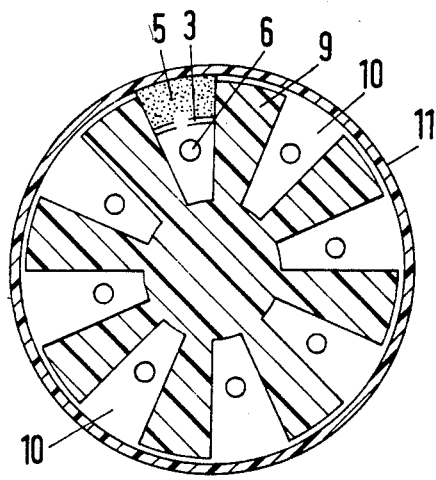
FIG. 4 is a cross sectional view of a further embodiment for a cable with a star-shaped core containing a signalling conductor according to the invention.

FIG. 4 shows still another embodiment of a cable which has a star-shaped core 9, in consequence of which axially running notches 10 are formed. A glass fibre 6 can be inserted in each of these notches 10, and at least one of the fibres 6 in one notch may comprise the signalling conductor. After the light guides 6 have been inserted and the swelling powder has been supplied, the star-shaped core 9 is surrounded by a perforated or porous sheath 11. The swelling powder 5 in the notch of the signalling conductor or conductors 6 can be applied to a substrate or not. The wave-shaped pattern 3 can be mounted either on a separate membrane between the light guide 6 and the swelling powder 5 or on the bottom of the notch 10.

It is self-evident that the idea of the invention can be realized in a large number of other embodiments.

While there is described above the principles of this invention in connection with specific apparatus, it is to be clearly understood that this description is made only by way of example and not as a limitation to the scope of this invention.

We claim:

1. A moisture signalling conductor comprising:
   (A) an elongated tubular element pervious to moisture and having a rib-shaped pattern pressure area therein,
   (B) a light guide in said tubular element, and
   (C) a swellable material in said tubular element which swellable material swells under the influence of moisture entering into said tubular element to deform and press said light guide against said pressure area to produce detectable attenuation in said light guide for indicating the location of said moisture in said tubular element.

2. A moisture signalling conductor according to claim 1 wherein said pressure area is provided with a wave-shaped pattern causing periodic microbending in said light guide when pressed against said pressure area.

3. A moisture signalling conductor according to claim 1 wherein said swellable material inserted in said tubular element has been applied to a substrate.

4. A moisture signalling conductor according to claim 3 wherein said substrate has a cross-section which is substantially round.

5. A moisture signalling conductor according to claim 1 wherein said tubular element comprises a membrane which is mounted as a separating wall between said swellable material and said light guide.

6. In a cable having a sheath pervious to moisture and a star-shaped cross-sectional core forming longitudinal notches, at least one of said notches containing:
   (A) a swellable material which swells under the influence of moisture,
   (B) a light guide, and
   (C) a rib-shaped pattern pressure area against which said light guide is pressed and deformed by the swelling of said swellable material to produce a detectable attenuation in a signal transmitted in said light guide for indicating the location of the moisture in said cable which caused said swellable material to swell.

* * * * *